(12) United States Patent
Zeng et al.

(10) Patent No.: US 12,390,142 B2
(45) Date of Patent: Aug. 19, 2025

(54) SYSTEMS AND METHODS FOR ELECTROCARDIOGRAPHIC MAPPING AND TARGET SITE IDENTIFICATION

(71) Applicant: CARDIOINSIGHT TECHNOLOGIES INC., Independence, OH (US)

(72) Inventors: Qingguo Zeng, Solon, OH (US); Timothy G. Laske, Shoreview, OH (US); Qing Lou, Solon, OH (US)

(73) Assignee: CARDIOINSIGHT TECHNOLOGIES INC., Independence, OH (US)

( * ) Notice: Subject to any disclaimer, the term of this patent is extended or adjusted under 35 U.S.C. 154(b) by 528 days.

(21) Appl. No.: 17/840,256

(22) Filed: Jun. 14, 2022

(65) Prior Publication Data

US 2023/0036977 A1 Feb. 2, 2023

Related U.S. Application Data

(60) Provisional application No. 63/228,405, filed on Aug. 2, 2021.

(51) Int. Cl.
*A61B 5/367* (2021.01)
*A61B 5/327* (2021.01)
(Continued)

(52) U.S. Cl.
CPC .............. *A61B 5/367* (2021.01); *A61B 5/327* (2021.01); *A61B 5/35* (2021.01); *A61B 34/10* (2016.02); *A61B 2034/107* (2016.02)

(58) Field of Classification Search
CPC ......... A61B 5/367; A61B 34/10; A61B 5/327; A61B 5/35
See application file for complete search history.

(56) References Cited

U.S. PATENT DOCUMENTS 10,932,863 B2 * 3/2021 Adler ................. A61B 18/1492
2014/0200467 A1 7/2014 Strom et al.
(Continued)

FOREIGN PATENT DOCUMENTS

WO 2017078757 A1 5/2017
WO 2017192294 A1 11/2017
WO 2019118640 A1 6/2019

OTHER PUBLICATIONS

Clifford G. Robinson, et al.; Phase I/II Trial of Electrophysiology-Guided Noninvasive Cardiac Radioablation for Ventricular Tachycardia; Circulation. Jan. 15, 2019; 139:313-321; DOI: 10/1161/CIRCULATIONAHA.118.038261.
(Continued)

*Primary Examiner* — David Bilodeau
(74) *Attorney, Agent, or Firm* — Tarolli, Sundheim, Covell & Tummino LLP

(57) ABSTRACT

In an example, a signal segment evaluator can be programmed to evaluate a morphology of at least one electrophysiological signal to identify a signal segment of interest. The morphology of the signal segment of interest can be indicative of an electrophysiological event of a patient during a respective time interval. A reconstruction engine can be programmed to reconstruct electrophysiological signals on a surface of interest within a body of the patient based on the electrophysiological signals measured from an outer surface of the patient and geometry data representing an anatomy of the patient. A map generator can be programmed to generate a map representing the reconstructed electrophysiological signals on the surface of interest for the respective time interval of the signal segment of interest. A target generator can be programmed to identify a target site within the patient's body based on the map for the electrophysiological event.

36 Claims, 5 Drawing Sheets

(51) Int. Cl.
    *A61B 5/35*     (2021.01)
    *A61B 34/10*    (2016.01)

(56) References Cited

U.S. PATENT DOCUMENTS

| | | | |
|---|---|---|---|
| 2015/0042646 A1* | 2/2015 | Comaniciu | G06T 7/12 |
| | | | 345/420 |
| 2015/0216438 A1* | 8/2015 | Bokan | A61B 5/316 |
| | | | 600/515 |
| 2018/0132743 A1* | 5/2018 | Markovitz | A61B 5/287 |
| 2018/0199847 A1* | 7/2018 | Markovitz | A61B 5/316 |
| 2018/0310850 A1 | 11/2018 | Zeng et al. | |
| 2019/0282112 A1* | 9/2019 | Jia | A61B 5/316 |
| 2019/0336023 A1* | 11/2019 | Lou | A61B 5/333 |
| 2021/0186351 A1* | 6/2021 | Govari | A61B 5/062 |
| 2022/0183609 A1* | 6/2022 | Handa | A61B 5/318 |

OTHER PUBLICATIONS

Parreira, Leonor, et al. "Successful ablation of premature ventricular contractions exclusively guided by epicardial and endocardial non-invasive mapping (ECGI) and confirmed by substrate mapping." Journal of Electrocardiology 62; Jul. 2020: 103-106.

Cuculich, Phillip S., et al. "Noninvasive cardiac radiation for ablation of ventricular tachycardia." New England Journal of Medicine 377.24; Dec. 14, 2017; 2325-2336.

Supplementary Appendix to Cuculich, Phillip S., et al.; "Noninvasive cardiac radiation for ablation of ventricular tachycardia." New England Journal of Medicine 377.24; Dec. 14, 2017; 2325-2336.

Applicant: Cardioinsight Technologies Inc.; "Systems and Methods for Electrocardiogramapping and Target Site Identification"; International Application No. PCT/US2022/039014 Filed Aug. 1, 2022; PCT International Search Report and Written Opinion; Mailed Oct. 25, 2022; 15 pgs.

\* cited by examiner

SYSTEMS AND METHODS FOR ELECTROCARDIOGRAPHIC MAPPING AND TARGET SITE IDENTIFICATION

CROSS REFERENCE TO RELATED APPLICATION

This application claims the benefit of U.S. Provisional Patent Application No. 63/228,405, filed 2 Aug. 2021, which is incorporated herein by reference in its entirety.

FIELD

The present technology relates to systems and methods for electrocardiographic mapping and target site identification.

BACKGROUND

Electrophysiological signals are sensed in a variety of applications, including electroencephalography, electrocardiography, electromyography, electrooculography, and the like. Electrocardiographic mapping (ECM) is a technology that is used to determine and display heart electrical information from sensed electrical signals. Cardiac ablation is a procedure used to remove or terminate a faulty electrical pathway from sections of a heart of those who are prone to developing cardiac arrhythmias. The ablation procedure can be classified by energy source, such as including radiofrequency ablation, radiation ablation and cryoablation to name a few.

SUMMARY

The techniques of this disclosure generally relate to systems and methods for electrocardiographic mapping and target site identification.

In one aspect, the present disclosure provides one or more non-transitory computer-readable media that include data and machine readable instructions that can be executed by a processor. The data can include electrophysiological data representing electrophysiological signals measured from an outer surface of a patient's body and geometry data representing an anatomy of the patient. The machine readable instructions can include a signal segment evaluator that can be programmed to evaluate a morphology of at least one of the electrophysiological signals to identify a signal segment of interest. The morphology of the signal segment of interest can be indicative of an electrophysiological event of the patient during a respective time interval. The machine readable instructions can include a reconstruction engine that can be programmed to reconstruct electrophysiological signals on a surface of interest within a body of the patient based on the electrophysiological signals and the geometry data, a map generator that can be programmed to generate a map representing the reconstructed electrophysiological signals on the surface of interest for the respective time interval of the signal segment of interest, and a target generator that can be programmed to identify a target site within the patient's body based on the map for the electrophysiological event.

In another aspect, the present disclosure provides a system that includes a plurality of sensors that can be configured to measure electrophysiological signals from an outer surface of a patient's body, memory that can be configured to store machine readable instructions and data comprising electrophysiological data representing the electrophysiological signals and geometry data representing an anatomy of the patient, and at least one processor that can be configured to access the memory and configured to execute the machine readable instructions. The machine readable instructions can include a signal segment evaluator that can be programmed to evaluate a morphology of at least one of the electrophysiological signals to identify a signal segment of interest. The morphology of the signal segment of interest can be indicative of an electrophysiological event of the patient during a respective time interval. The machine readable instructions can include a reconstruction engine that can be programmed to reconstruct electrophysiological signals on a surface of interest within the patient's body based on the electrophysiological data representing the electrophysiological signals for the respective time interval of the signal segment of interest, a map generator that can be programmed to generate a map representing the reconstructed electrophysiological signals on the surface of interest for the respective time interval of the signal segment of interest, and target generator that can be programmed to identify a target site within the patient's body based on the map for the electrophysiological event.

In a further aspect, the present disclosure provides a method that includes evaluating a morphology of at least one electrophysiological signal of a plurality of electrophysiological signals measured from an outer surface of a patient's body to identify first and second signal segments of interest. The morphology of each of the first and second signal segments of interest can be indicative of an electrophysiological event of the patient during one of a first time interval and a second time interval. The method can include reconstructing electrophysiological signals on a surface of interest within a body of the patient based on the electrophysiological signals and geometry data. The geometry data can represent an anatomy of the patient. The method can include generating a first map representing the reconstructed electrophysiological signals on the surface of interest for the first time interval of the first signal segment of interest, generating a second map representing the reconstructed electrophysiological signals on the surface of interest for the second time interval of the second signal segment of interest, and identifying a target site within the patient's body based on the first and second maps for the electrophysiological event.

The details of one or more aspects of the disclosure are set forth in the accompanying drawings and the description below. Other features, objects, and advantages of the techniques described in this disclosure will be apparent from the description and drawings, and from the claims.

DETAILED DESCRIPTION

Figure 1:
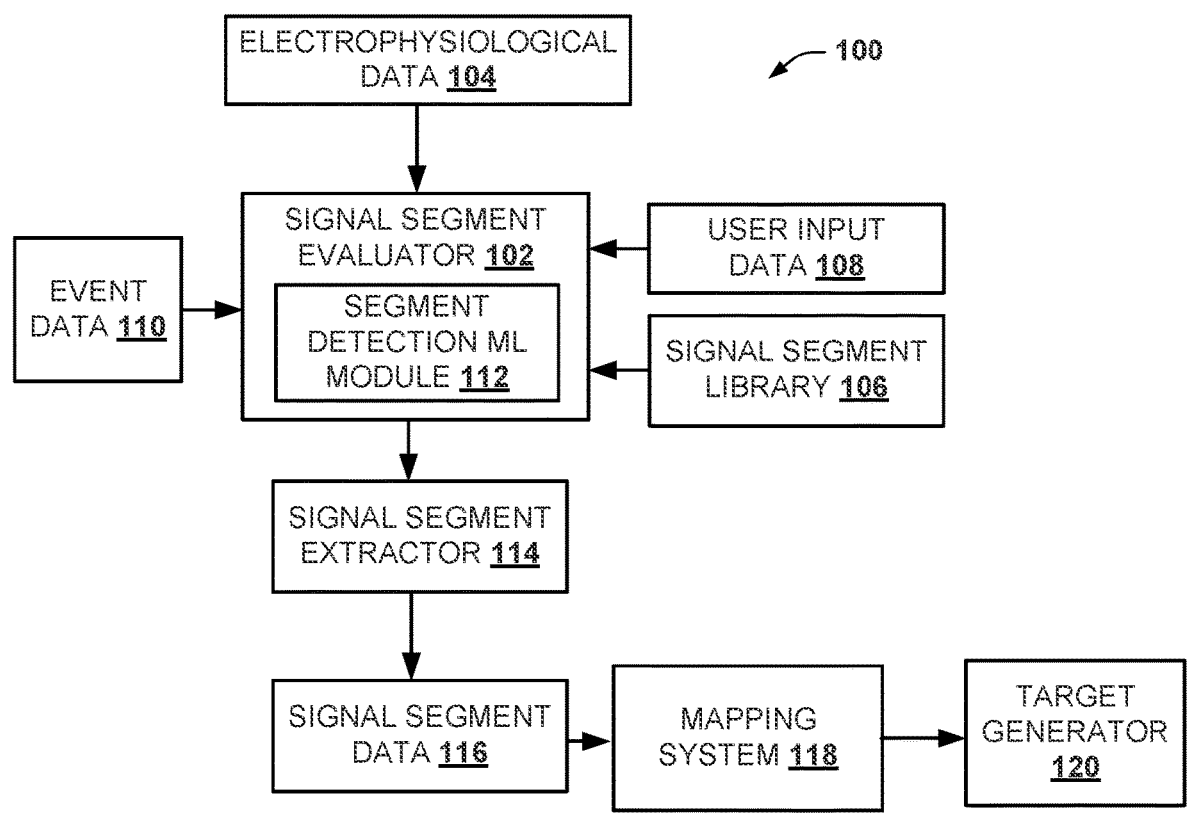
FIG. 1 is a block diagram of a target site identification system.

This disclosure relates to systems and methods for electrocardiographic mapping and target site identification, such as for treatment planning. In some existing approaches, electrocardiographic imaging (ECGI) is used in electrophysiology (EP) labs to diagnose and help plan treatment for arrhythmogenic activity, such as tachycardia or bradycardia. For example, noninvasive cardiac radio ablation can be implemented as an EP-guided procedure. At the outset of an ablation procedure, an EP study is performed to assess a patient's heart functionality for mapping of cardiac electrical activity. An ECGI map is constructed based on the mapping and evaluated (e.g., automatically by machine-readable instructions and/or by a clinician) in combination with imaging data of a heart from an imaging modality to identify potential treatment sites. A target volume thus can be identified based on the ECGI map and the imaging data. The patient is transported to a radiation site and images are captured of the patient. The target volume is combined with the images of the heart to provide a target site for the delivery of radiation to the patient. In some existing approaches, the identification of potential treatment sites is a manual process that relies on the clinician's judgment in identifying each treatment site. Thus, the efficacy of ablation of arrhythmias within the patient is highly dependent on the accuracy in identifying arrhythmia origin sites.

Systems and methods are disclosed herein for target site identification for non-invasive ablation therapy. According to the systems and methods disclosed herein, a target site on the patient's heart can be identified automatically providing for an improved approach for target identification on the patient's heart, and thus in some instances, without input from the clinician. As such, the systems and methods disclosed herein can streamline existing non-invasive ablation treatment procedures and provide for a systematic approach for target site identification for non-invasive radiotherapy treatment. While many examples herein are described in the context of cardiac electrical signals, it is to be understood that the approaches disclosed herein are equally applicable to other electrophysiological signals, such as electroencephalography, electromyography, electrooculography, and the like.

As disclosed herein, a signal segmentation system can be configured to evaluate a morphology of one or more electrophysiological signals (e.g., one or more intervals of a signal waveform) of electrophysiological signals measured non-invasively from a body surface of the patient to identify a signal segment of interest. The signal segment of interest can represent an electrophysiological event (e.g., an arrhythmia) of the patient during a respective time interval. The signal segment of interest and/or the respective time interval for the signal segment of interest can be saved in memory as signal segment data. A mapping system can include instructions programmed to implement an inverse solution. The inverse solution can be implemented to reconstruct electrophysiological signals on a surface of interest within a body of a patient based on the signal segment data and/or the electrophysiological signal data, and geometry data. The geometry data can represent an anatomy of the patient in a three-dimensional coordinate system, including spatial geometry of the patient's heart and torso (e.g., thorax) where the electrophysiological signals are measured from the patient's body. The mapping system is configured to generate a map representing the reconstructed electrophysiological signals on the surface of interest, including for the respective time interval of the identified signal segment of interest. A target generator can be used to identify each target site within the patient's body based on the map for one or more electrophysiological events. Each target site on the map can be differentiated from surrounding regions of the surface of interest.

In some examples, the mapping system can be configured to generate multiple different maps representing the reconstructed electrophysiological signals on the surface of interest for the respective time interval of the identified signal segment of interest. The different maps may be different types of maps (e.g., potential maps, phase maps, butterfly maps and the like) generated for the respective time interval of the identified signal segment. The target generator can be configured to identify electrophysiological event features from one or more of the respective maps. The target generator can be configured to identify the target site within the patient's body based on the identified electrophysiological event features. In some examples, the mapping system is configured to generate maps representing the reconstructed electrophysiological signals on the surface of interest for multiple different time intervals of respective identified signal segments of interest. The target generator can be configured to identify one or more respective target sites based on the electrophysiological event features in each map for each segment of interest over the respective different time intervals. In some examples, the target generator can generate a description (e.g., spatial coordinates or a volume boundary) of the identified target site to a map fusion engine. The map fusion engine can be configured to average the maps to average or otherwise mathematically combine the identified respective target sites in the respective maps to provide a composite target site for the respective electrophysiological events.

FIG. 1 is an example of a system 100 for identifying a target site. The system 100 can be implemented as hardware (e.g., circuit and/or devices), software (e.g., a non-transitory medium having machine-readable instructions), or a combination of hardware and software. The system 100 can be configured to evaluate electrophysiological signals to identify signal segments representing an electrophysiological event of a patient. The system 100 can include a signal segment evaluator 102. The signal segment evaluator 102 can be configured to identify a signal segment of interest based on electrophysiological data 104.

The electrophysiological data 104 can be stored in a memory and can be representative of electrophysiological signals obtained by sensors. The sensors can be applied to measure an electrical activity of an anatomical structure of the patient non-invasively. For example, the sensors may be positioned over a patient's body surface such as the patient's thorax (e.g., for electrocardiography). Examples of sensors that may be utilized to acquire the electrophysiological signals are disclosed in U.S. Pat. No. 9,549,683. Additionally, or alternatively, other sensors (e.g., a twelve lead ECG or the like) may be used to measure the electrophysiological signals from the patient's body. In some examples, the electrophysiological signals are acquired in real-time, such as during a procedure or study. For example, the electrophysiological data 104 can correspond to a real time data flow that can be acquired by non-invasive (e.g., body surface) sensors during a procedure such as during an electrophysiological study as well as during a treatment procedure that can include cardiac ablation. In other examples, the electrophysiological data 104 includes electrophysiological measurements acquired over an extended period of time prior to a procedure, such as by a halter monitoring system or the like.

In some examples, the signal segment evaluator 102 can be configured to evaluate each electrophysiological signal of the electrophysiological data 104 to identify each signal segment of interest. For example, the signal segment evaluator 102 is configured to evaluate a morphology of an electrophysiological signal (e.g., an interval of a respective signal waveform) to identify the signal segment of interest. The signal segment evaluator 102 can be configured to evaluate a morphology of respective waveforms in each of a plurality of bipolar electrophysiological signals acquired over one or more time intervals to identify the signal segment of interest. Additionally, or alternatively, the segment evaluator 102 can be configured to evaluate a morphology of respective waveforms in each of a plurality of unipolar electrophysiological signals acquired over one or more time intervals to identify the signal segment of interest. The type of signal may depend on the type of sensors being used to measure the electrophysiological signals from the patient's body. The term "signal segment of interest" as used herein can refer to a portion of an electrophysiological signal (e.g., from one or more beats) having a morphology that is indicative of an electrophysiological event of the patient during a respective time interval. By way of example, the electrophysiological event can include any arrhythmia event, such as premature ventricular contraction (PVC) events, ventricular tachycardia (VT) events atria tachycardia (AT) events, premature atria contraction (PAC), Wolff-Parkinson-White syndrome (WPW) events, catecholaminergic polymorphic ventricular tachycardia (CPVT), Brugada syndrome, and idiopathic ventricular fibrillation, atrial fibrillation, bradycardia events and others. In some examples, the signal segment evaluator 102 can be configured to evaluate each electrophysiological signal based on a signal segment library 106 to identify each signal segment of interest therein.

As a further example, the signal segment library 106 is stored in memory with data describing each of a plurality of different types of electrophysiological events. By way of example, the plurality of different types of biological events include one of a plurality of different types of PVC and/or VT events. In some examples, the signal segment library 106 can include electrophysiological event templates, which may include generic event templates and/or patient-specific event templates. Each electrophysiological event template can include data characterizing a morphology of a respective portion of an electrophysiological signal (e.g., a waveform) representing a respective electrophysiological event.

In some examples, the signal segment evaluator 102 can be configured to evaluate a morphology of each remaining electrophysiological signal of the electrophysiological signals to identify a respective signal segment of interest from each remaining electrophysiological signals. This can result in multiple signal segments of interest being identified from different respective signals measured from different spatial locations across the patient's body. The morphology of each remaining signal segment of interest can be indicative of the electrophysiological event of the patient during the respective time interval, which may include the same or different time intervals.

In some examples, the signal segment evaluator 102 can be configured to apply a moving window to the electrophysiological signal to sample a portion (e.g., a time interval) of the electrophysiological signal. The moving window can have a defined window size corresponding to a sampling window size for a time interval. The sampling window size can be defined based on user input data 108, such as to select a start and end time for the time interval. The signal segment evaluator 102 can be configured to slide the moving window across each electrophysiological signal and compare each sampled portion of each electrophysiological signal to the signal segment library 106. For example, the signal segment evaluator 102 can be configured to compare each sampled portion of the electrophysiological signal to each electrophysiological event template. A user may select one or more electrophysiological event templates (in response to a user input) to apply to the electrophysiological signals so that the user can specify the type or types of electrophysiological events that can be identified. Alternatively, a full set of available templates can be applied to search the signals for signal segments matching any of the event types.

The signal segment evaluator 102 can be configured to identify (e.g., tag) each sampled portion of the electrophysiological signal that matches a respective electrophysiological event template of the signal segment library 106 as a respective signal segment of interest. In some examples, the signal segment evaluator 102 can be configured to identify each signal segment of interest in the electrophysiological signal based on the user input data 108. For example, the user input data 108 can identify a time interval that includes the signal segment of interest. Because a given template may specify a respective type of electrophysiological event (e.g., PVC, VT tachycardia, or the like), the signal segment evaluator 102 can append metadata to respective signal segments of interest that describe the corresponding event type. Thus, the signal segment of interest may be selected by a user (e.g., in response to a user input) or automatically (e.g., based on the signal segment library 106 or electrophysiological event data 110, as disclosed herein).

In some examples, the signal segment evaluator 102 is configured to identify the signal segment of interest based on the electrophysiological event data 110. The electrophysiological event data 110 can be indicative of an instance of time at which the electrophysiological event occurred, such as may be an event that was induced on the patient. The electrophysiological event data 110 can identify an inducement time interval having a start time indicative of when the electrophysiological event was induced and an end time indicative of when the induced electrophysiological event terminated. The electrophysiological event can be induced by a device implanted in the body of the patient or be applied externally to an outer surface of the patient's body. By way of example, the implanted device can be an implantable cardioverter-defibrillator (ICD). In some examples, the electrophysiological event can be terminated by the device, such as in response to a user input instruction or after a defined duration for the event.

By way of example, the signal segment evaluator 102 can be configured to select the portion of the electrophysiological signal as the signal segment of interest based on the inducement time interval of the electrophysiological event data 110. For example, each electrophysiological signal of the electrophysiological data 104 can include time stamp information. Appropriate time stamps can be utilized for indexing each electrophysiological signal over time, which can be stored as timing data with each sample of the acquired electrophysiological signals, to facilitate evaluation and analysis thereof. The signal segment evaluator 102 can be configured to compare the inducement time interval for the electrophysiological event as specified by the electrophysiological event data 110 to the time stamps of the electrophysiological signal to identify the respective time interval for the portion of the electrophysiological signal as the signal segment of interest.

In some examples, the signal segment evaluator 102 can be configured to identify a respective time stamp or other timing data to specify a respective time interval for the electrophysiological signal based on the time at which the electrophysiological was induced. The respective time stamp can correspond to an instance of time at which the electrophysiological event was induced within the patient. The signal segment evaluator 102 can be configured to select the portion of the electrophysiological signal as the signal segment of interest for the respective interval of time beginning at or about the respective time stamp. The respective interval of time can correspond to a period of time that can be defined by the user input data 108. In some examples, the respective interval of time is similar to the sampling window size of the moving window.

In some examples, the signal segment evaluator 102 can include a segment detection machine learning (ML) module 112. For example, the segment detection ML module 112 can be generated by a respective ML algorithm. The ML algorithm can include of an artificial neural network (ANN) algorithm, a support-vector machine (SVM) algorithm, a decision tree algorithm, a recurrent neural network (RNN) algorithm, and a convolutional neural network (CNN) algorithm. In other examples, a different ML algorithm can be used for generating the segment detection ML module 112. The ML algorithm can be trained on prior identified signal segments of interest from electrophysiological signals that represent different electrophysiological events during a respective time interval to provide the segment detection ML module 112. The segment detection ML module 112 can be configured to process the electrophysiological data 104 to identify each signal segment of interest. As a further example, the segment detection ML module 112 can be configured to evaluate each identified signal segment of interest to identify similar signal segments of interests. The signal segment evaluator 102 can be configured to group signal segments of interest that are highly correlated (e.g., similar) and label the grouped signal segment of interest with a first label. For signal segments of interest that are not similar to other signal segments of interest, the signal segments of interest can be labeled with a second label. The first and second labels can be employed for target site identification as described herein. The first label can identify a first signal segment type (e.g., a type of VT), and the second label can identify a second signal segment type (e.g., a different type of VT).

In other examples, the signal segment evaluator 102 can implement a nearest neighbor algorithm, such as a KD tree algorithm to identify each signal segment of interest. For example, the nearest neighbor algorithm can be applied to the electrophysiological data 104 to identify each signal segment of interest. In further examples, the segment detection ML module 112 can be configured to implement a principal component analysis (PCA) based on the electrophysiological data 104 to identify each signal segment of interest.

In some examples, the system 100 includes a signal segment extractor 114. The signal segment extractor 114 can be configured to extract each signal segment of interest. For example, the signal segment evaluator 102 can be configured to provide segment extraction data to the signal segment extractor 114. The segment extraction data can identify the respective time interval (e.g., a duration and/or start and end times) of each signal segment of interest from the electrophysiological signals identified by the signal segment evaluator 102. The signal segment extractor 114 can be configured to extract each signal segment of interest based on the segment extraction data. The signal segment extractor 114 can be configured to generate signal segment data 116 that includes each signal segment of interest extracted from each electrophysiological signal. In some examples, the signal segment data 116 includes timing information identifying the respective time interval for each signal segment of interest.

As disclosed herein, the signal segment data 116 can be used for reconstruction of the electrical activity across a surface of interest within the patient's body for target site identification. For example, the signal segment data 116 can be provided to a mapping system 118. The mapping system 118 can be configured to reconstruct electrophysiological signals on the surface of interest, such as by solving the inverse problem, based on the electrophysiological signals and geometry data, including for the respective time interval of the signal segment of interest. In some examples, the mapping system 118 generates one or more maps that are displayed to the user (e.g., on a screen or other display device).

The system 100 can include a target generator 120. The target generator 120 can be programmed to identify a target site within the patient's body based on the map generated (by the mapping system 118) for one or more identified electrophysiological events. In some examples, the target generator 120 is programmed to tag each identified target with a corresponding label (e.g., one of the first and second labels) for delivery of a therapy, such as described herein. Accordingly, the target site on the patient's heart can be identified automatically by the system 100 based on electrophysiological signals reconstructed on the surface of interest and according to the identified electrophysiological event. The system 100 streamlines existing non-invasive ablation treatment procedures by providing a systematic approach for target site identification. Thus, by identifying the target site based on the map representing the reconstructed electrophysiological signals on the surface of interest for the respective time interval of the signal segment of interest, treatment planning, which can include non-invasive radiotherapy treatment, can be facilitated.

Figure 2:
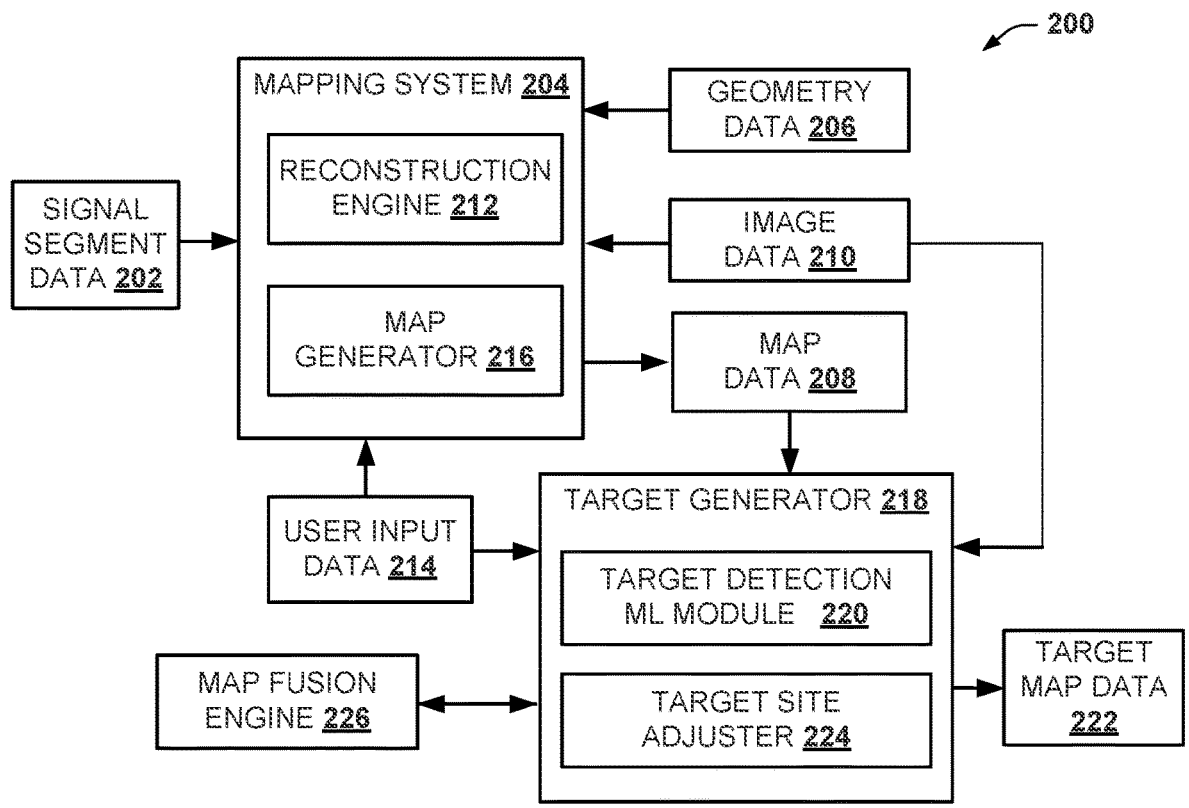
FIG. 2 is a block diagram of another target site identification system.

FIG. 2 is an example of a system 200 for identifying a target site within a patient. The system 200 can be implemented as hardware (e.g., circuit and/or devices), software (e.g., a non-transitory medium having machine-readable instructions), or a combination of hardware and software. In some examples, the signal segment data 202 can be provided to a mapping system 204 of the system 200. The signal segment data 202 can correspond to the signal segment data 116 and the mapping system 204 can correspond to the mapping system 118, as shown in FIG. 1. As such, in some examples, reference can be made to the example of FIG. 1 in the following description of the example of FIG. 2. As disclosed herein, the signal segment data 202 can identify each signal segment of interest from one or more electrophysiological signals measured from an outer surface of a patient's body. A morphology of each signal segment of interest can be indicative of an electrophysiological event of the patient, such as disclosed herein. In some examples, the signal segment data 202 can specify a respective time interval for each signal segment of interest.

For example, the signal segment data 202 is provided to a mapping system 204. In some examples, the mapping system 204 can be configured to combine the signal segment data 202 with geometry data 206 to generate map data 208. The map data 208 can include a map that can represent reconstructed electrophysiological signals spatially and temporally on a surface of interest within a body of a patient, including for the respective time interval of a signal segment of interest identified by the system 100. In some examples, the mapping system 204 can be configured to receive the electrophysiological data 104 representing electrophysiological signals measured from the outer surface of the patient's body. The mapping system 204 can be configured to provide the map data 208 based on the signal segment data 202, electrophysiological data 104, and the geometry data 206, as disclosed herein.

The signal segment data 202 and/or the electrophysiological data 104 can be stored with the geometry data 206 in memory (e.g., one or more non-transitory computer readable media) as electroanatomic data that describes the electrical activity at a plurality of anatomical locations (e.g., nodes) across the surface of interest (e.g., in three-dimensional space) for the respective time interval. The anatomical locations can be represented as nodes distributed (e.g., an even distribution) over the surface of interest, represented by the geometry data 206. The surface of interest can be a surface of an anatomical structure, such as a tissue of a patient (e.g., human or other animal). In some examples, the patient tissue can be cardiac tissue, such that the surface of interest corresponds to an epicardial surface, an endocardial surface, or another cardiac envelope. The surface of interest can be patient-specific (e.g., based on imaging data for the patient), it can be a generic model of the surface or it can be a hybrid version of a model that is customized based on patient-specific data (e.g., imaging data, patient measurements, reconstructed data, and/or the like). As disclosed herein, the surface of interest can be defined by the geometry data 206 that is stored in the memory.

In some examples, the geometry data 206 can represent a two-dimensional or a three-dimensional surface for the patient. For example, a measurement surface can include a body surface (e.g., an outer surface of the thorax or portion thereof) where sensors are positioned to measure electrical activity. In other examples, the surface of interest can be a surface of internal tissue or a computed envelope having a prescribed position relative to certain internal tissue. Depending on the surface of interest for which the signal segment data 202 or the electrophysiological data 104 has been provided, the geometry data 206 can correspond to actual patient anatomical geometry, a preprogrammed generic model, or a hybrid thereof (e.g., a model that is modified based on patient anatomy).

By way of example, the geometry data 206 can be derived from image data 210 generated by an imaging modality. Examples of imaging modalities include ultrasound, computed tomography (CT), 3D Rotational angiography (3DRA), magnetic resonance imaging (MRI), x-ray, positron emission tomography (PET), fluoroscopy, and the like. Such imaging can be performed separately (e.g., before or after) the measurements utilized to generate electrical data (e.g., the electrophysiological data 104, as shown in FIG. 1). By way of further example, the geometry data 206 can be acquired using nearly any imaging modality based on which a corresponding representation of a geometrical surface can be constructed, such as disclosed herein. Such imaging may be performed concurrently with the recording of the electrophysiological signals that are utilized to generate the electrophysiological data 104 or the imaging can be performed separately (e.g., before or after the electrophysiological data 104 has been acquired).

In some examples, the mapping system 204 is configured to derive the geometry data 206 from the image data 210. As disclosed herein, the surface of interest can correspond to a three-dimensional surface geometry corresponding to a patient's heart, which surface can be epicardial and/or endocardial. Alternatively or additionally, the cardiac envelope can correspond to a geometric surface that resides between the epicardial surface of a patient's heart and the surface of the patient's body where a sensor array has been positioned. Additionally, the geometry data 206 that is utilized by the mapping system 204 can correspond to actual patient anatomical geometry, a preprogrammed generic model, or a combination thereof (e.g., a model that is modified based on patient anatomy).

As an example, the geometry data 206 may be in the form of a graphical representation of the patient's torso, such as the image data 210 acquired for the patient. Image processing, which in some examples, can be implemented by the mapping system 204, can include extraction and segmentation of anatomical features, including one or more organs and other structures, from a digital image set corresponding to the image data 210. Additionally, a location for each of the sensors in the sensor array can be included in the geometry data 206, such as by acquiring the image while the sensors are disposed on the patient and identifying the electrode locations in a coordinate system through appropriate extraction and segmentation. Other non-imaging based techniques can also be utilized to obtain the position of the sensors in the sensor array, such as a digitizer or manual measurements.

In some examples, the geometry data 206 can correspond to a mathematical model, such as can be a generic model or a model that has been constructed based on the image data 210 for the patient. Appropriate anatomical or other landmarks, including locations for the sensors in the sensor array, can be identified in the geometry data 206 to facilitate registration of the signal segment data 202 or the electrophysiological data 104 and performing the inverse method thereon. The identification of such landmarks can be done manually (e.g., by a person via image editing software) or automatically (e.g., via image processing techniques), in some examples, can be implemented by the mapping system 204.

In some examples, the mapping system 204 can include a reconstruction engine 212. The reconstruction engine 212 can be configured to compute an inverse solution to reconstruct electrophysiological signals on the surface of interest within the body of the patient based on the electrophysiological data 104, signal segment data 202, and the geometry data 206. For example, the reconstruction engine 212 can be configured to combine the electrophysiological data 104, the signal segment data 202 and the geometry data 206 through an inverse calculation. Examples of solutions to the inverse problem can include a boundary element method (BEM) or a method of fundamental solution (MFS). In some examples, the inverse calculation can employ a transformation matrix to reconstruct electrical activity sensed on the patient's body onto an anatomic envelope, such as the epicardial surface, the endocardial surface or other envelope. Examples of inverse algorithms that can be utilized to implement the inverse solution by the reconstruction engine 212 include those disclosed in U.S. Pat. Nos. 7,983,743 and 6,772,004. The reconstruction engine 212 thus can reconstruct a body surface electrical activity measured via the sensors (e.g., the sensor array) on a body of the patient onto a multitude of locations on a cardiac envelope corresponding to a sub-region of the heart for the electrophysiological event.

In some examples, the reconstruction engine 212 can be configured to reconstruct the electrophysiological signals on the surface of interest within the patient's body based on the electrophysiological data 104 representing the electrophysiological signals for the respective time interval of the signal segment of interest as specified by the signal segment data 202, and the geometry data 206. Thus, in some examples, the reconstruction engine 212 can be configured to reconstruct a portion of the electrophysiological signals over a time interval corresponding to the respective time interval of the signal segment of interest. In some examples, the respective time interval can be identified by the signal segment data 202 and can be used by the reconstruction engine 212 to reconstruct the portion of the electrophysiological signals over the time interval corresponding to the respective time interval of the signal segment of interest. The reconstruction engine 212 can be configured to reconstruct electrophysiological signals on the surface of interest based on each signal segment of interest that has been identified, as represented by the signal segment data 202.

In some examples, the reconstruction engine 212 can be configured to compute the inverse solution based on tissue scar information for the surface of interest. For example, the mapping system (or a different system) can be configured to evaluate the image data 210 to identify one or more regions on the anatomical structure that are scarred or damaged. The reconstruction engine 212 can be configured to compute the inverse solution based on the identified region on the surface of interest that are scarred or damaged from the image data 210. For example, the reconstruction engine 212 can be configured to compute the inverse solution based on a fiber orientation and/or a wall thickness obtained from the image data 210. For example, the mapping system 204 can be configured to evaluate the image data 210 to determine the fiber orientation and/or a wall thickness for the region of the anatomical structure. In an example, the reconstruction engine 212 can be configured to compute the inverse solution based on user input data 214. For example, the user input data 214 can identify the one or more regions on the anatomical structure that have been ablated. Thus, the reconstruction engine 212 can be configured to compute the inverse solution based on prior ablation information for the anatomical structure of the patient.

As a further example, the mapping system 204 is configured to compute a map (e.g., one or more cardiac maps) based on the reconstructed electrophysiological signals on the surface of interest within the body. To compute the map, the mapping system 204 can include a map generator 216. The map generator 216 can be configured to generate the map representing the reconstructed electrophysiological signals on the surface of interest for the respective time interval of the identified signal segment of interest. Thus, the map generator 216 can be configured to reconstruct the electrophysiological signals on the surface of interest rendered on an anatomical model of the surface of interest. The map generator 216 further may compute or derive one or more maps from the reconstructed electrophysiological signals (e.g., reconstructed electrogram signals) to characterize features of the reconstructed signals across the surface of interest for the respective time interval of the identified signal segment of interest. For example, the map can include a potential map, a butterfly map (e.g., graphically representing a common conduction pathway), a phase map, a propagation map, a potential map, an activation map and/or another type of map derived from the reconstructed electrophysiological signals or the body surface electrophysiological measurements (e.g., a cycle length map, a dominant frequency map, etc.). In other examples, a different cardiac can be computed as disclosed herein. The mapping system 204 can be configured to provide the map (or maps) as the map data 208. Examples of butterfly maps that can be generated by the map generator 216 include those disclosed in U.S. Pat. No. 10,806,359.

In some examples, the map data 208 can be provided to (or accessed by) a target generator 218. The target generator 218 can be similar to the target generator 120, as shown in FIG. 1. The target generator 218 can be configured to identify a target site within the body of the patient based on the map data 208 corresponding to the map for the electrophysiological event, which is represented by the respective time interval of the identified signal segment of interest. The target generator 218 can be configured to evaluate the map data 208 and identify a region on the surface of interest as the target site. The region identified as the target site by the target generator 218 can correspond to a portion of the surface of interest that includes the reconstructed electrophysiological signals on the surface of interest for a respective time interval of the identified signal segment of interest. As disclosed herein, the target site can specify a location for delivery of a therapy to treat the patient.

In some examples, the target generator 218 can be configured to identify each target site on the map based on the user input data 214. For example, the user input data 214 can specify each target site on the surface of interest. In some examples, the target generator 218 can include a target detection machine learning (ML) module 220. The target detection ML module 220 can be trained on prior map data that includes one or more maps of reconstructed electrophysiological signals on a surface of interest with identified target sites. The target detection ML module 220 can be generated by one of the ML algorithms disclosed herein or by another type of ML algorithm. The target detection ML module 220 can be configured to process the map data 208 to identify each target site on the surface of interest.

In some examples, the target generator 218 can be configured to denote each target site on the surface of interest to differentiate the target site from surrounding regions on the surface of interest and/or other target sites on the surface of interest. For example, each target site can be denoted with a corresponding color from a color scale or other scale to distinguish the target site on the map. In some examples, the target detection ML module 220 can be trained to distinguish each target site on the map and provide a corresponding tag identifying a type of electrophysiological event for each tagged target site.

The target generator 218 can be configured to generate target map data 222 that includes the map with each target site (or candidate target site) graphically differentiated. In some examples, the target map data 222 can identify each target site. For example, the surface of interest (e.g., geometric surface) can be represented as a mesh that includes a plurality of nodes interconnected by edges to define the mesh. The target generator 218 thus can generate the target map data 222 identifying the target site as one or more nodes of the plurality of nodes of the mesh. In some examples, the surface of interest can be represented by a mesh that includes a collection of vertices that define a plurality of polygons forming the surface of interest. Each polygon can include three or more vertices, such that adjacent vertices define edges that surround a face of each respective polygon. The target generator 218 can generate the target map data 222 identifying the target site as a region (or as a centroid of the region) enclosed by one or more polygons of the plurality of polygons.

As a further example, the target generator 218 can be configured to provide the map data 208 to a visualization engine, which can be configured to render the map data 208 on a display to provide a visualization of each target site and tagging information identify each type of target site. A user can employ an input device (e.g., a keyboard, a mouse, and the like) to select each target site as a candidate target site based on the rendering on the display. In some examples, the target generator 218 can be configured to generate target map data 222.

In some examples, the target generator 218 can include a target site adjuster 224. The target site adjuster 224 can be configured to update the target site (or the candidate target site) to an updated target site based on adjustment criteria. For example, the adjustment criteria may include one of the fiber orientation and the wall thickness for the region of the anatomical structure, such as computed from the image data 210. The target site adjuster 224 can be configured to adjust the target site to the updated target site by compensating for propagation of electrical signals through tissue based on the fiber orientation and/or the wall thickness. Because the target generator 218 can be configured to determine the target site based on the fiber orientation and/or the wall thickness an accuracy of the therapy delivered to the patient can be improved by identifying more critical sites on the surface of interest that require therapy (e.g., ablation). The target generator 218 can be configured to generate the target map data 222 characterizing each updated target site In some examples, the mapping system 204 is configured to generate a plurality of different types of maps (e.g., cardiac maps) representing the reconstructed electrophysiological signals on the surface of interest for the respective time interval of the signal segment of interest. The target generator 218 can be configured to identify electrophysiological event features from each of the plurality of different types of maps. For example, the electrophysiological event features can include a left ventricular outflow tract (LVOT) tachycardia event, a right ventricular outflow tract (RVOT) tachycardia event, or a great cardiac vein (GCV) tachycardia event. For example, the target generator 218 can include an ML module that can be trained to identify electrophysiological event features based on a respective map provided by the mapping system 204. As an example, the target generator 218 can include a CNN module or another type of deep learning algorithm that can be trained to identify (e.g., classify) tachycardia events originating from the left/right VOT and/or the GCV based on a phase map provided by the mapping system 204. The target generator 218 further can be configured to identify the target site within the patient's body based on one or more identified electrophysiological event features. The target generator 218 can be configured to provide the identified target site as the target map data 222.

In some examples, the reconstruction engine 212 can be configured to reconstruct electrophysiological signals on the surface of interest within the body of the patient based on the electrophysiological data 104 representing the electrophysiological signals for a first time interval of a first signal segment of interest. The reconstruction engine 212 can be configured to reconstruct electrophysiological signals on the surface of interest within the body of the patient based on the electrophysiological data 104 representing the electrophysiological signals for a second time interval of a second signal segment of interest. The first and second signal segments of interest can be identified by the system 100, as shown in FIG. 1, and there can be any number of respective signal segments of interest.

The map generator 216 can be configured to generate a first map representing the reconstructed electrophysiological signals on the surface of interest for the first time interval of the first signal segment of interest. The map generator 216 can be configured to generate a second map representing the reconstructed electrophysiological signals on the surface of interest for the second time interval of the second signal segment of interest. The target generator 218 can be configured to evaluate each of the first and second maps to identify and one or more target sites in a same or similar manner as disclosed herein. The target generator may identify a single target site based on the evaluation of the first and second maps. Alternatively, the target generator may identify multiple target sites based on such evaluation.

In some examples, the system 200 can include a map fusion engine 226. In some examples, the map generator 216 includes the map fusion engine 226. The map fusion engine 226 can be configured to average the first and second maps (or any set of two or more maps) to provide an average or composite map. For example, the map fusion engine 226 can average respective pixels from the first and second maps to provide the composite map. In other examples, a different averaging technique can be used that can be based on a red-green-blue (RGB) model or a hue, saturation, value (HSV) model. By way of further example, the map fusion engine 226 can normalize the first map according to a first color channel (e.g., red channel) of the RGB model and the second map can be normalized according to a second color channel (e.g., blue or green channel) of the RGB model. The map fusion engine 226 can combine the normalized first and second maps to provide the composite map. In other examples, the map fusion engine 226 can employ the HSV model to represent different components from each of the first and second maps. The map fusion engine 226 can be configured to combine the first and second maps with components represented according to the HSV model to provide the composite map. Thus, the map fusion engine 226 can be configured to combine two or more maps computed based on different signal segments of interest over different time intervals to generate a fused map. Alternatively, or additionally, the fusion engine can be programmed to average (or other mathematical or statistical calculation on) the target sites derived from any two more maps to provide a composite target site for the electrophysiological event. By averaging reconstructed electrophysiological signals on the surface of interest of each map or target site derived from such maps reduces or minimizes variances or noise in the reconstructed electrophysiological signals facilitating more accurate target identification via the composite target site. The target map data 222 can include the fused map with each target site being differentiated, such as disclosed herein. In some examples, the target map data 222 can identify the composite target site. As disclosed herein, the target map data 222 can be used to specify a location (e.g., a point or coordinates thereof) or a target volume in the patient's body for the delivery of the therapy or other intervention.

Figure 3:
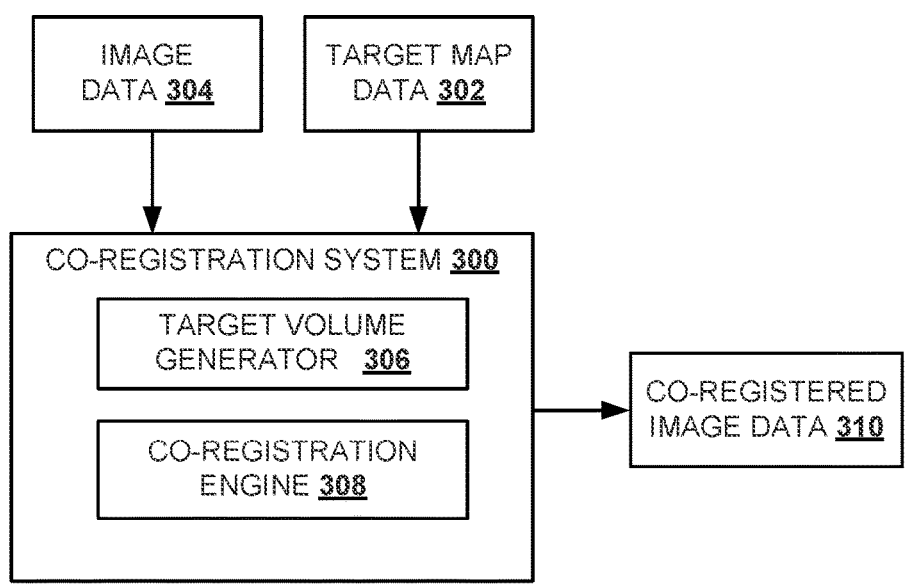
FIG. 3 is a block diagram of a target co-registration system.

FIG. 3 is an example of an image-target registration system 300. The image-target registration system 300 can be implemented as hardware (e.g., circuit and/or devices), software (e.g., a non-transitory medium having machine-readable instructions), or a combination of hardware and software. The image-target registration system 300 can be configured to register a target volume computed based on target map data 302 with image data 304 provided by an imaging modality. In an example, the image data 304 can be generated by any image modality and can include one or more images of an anatomical structure of a patient, such as a heart. In some examples, the one or more images are respiratory correlated (e.g., a four dimensional CT image). For example, the target map data 302 can correspond to or be derived based on the target map data 222, as shown in FIG. 2. Therefore, reference can be made to the example of FIG. 2 in the following description of the example of FIG. 3. The target map data 222 can include a map representing reconstructed electrophysiological signals on a surface of interest of the anatomical structure for each target site (or candidate target site), such as disclosed herein.

The image-target registration system 300 can employ a target volume generator 306. The target volume generator 306 can be configured to generate a spatial volume target site for each target site based on the target map data 302. In some examples, the target volume generator 306 can be configured to generate a respective the volume target site based on the image data 304 and each identified target site. In some examples, the image-target registration system 300 includes a co-registration engine 308. The co-registration engine 308 can be configured to register the volume target site in an image spatial domain of the image data 304 to provide co-registered image data 310. For example, the co-registration engine 308 can be configured to transfer the volume target site onto the coordinate system of one or more images defined by the image data 304 to provide co-registered image data 310. In some examples, the co-registration engine 308 can be configured to extract and segment the anatomical structure from the image data 304. The co-registration engine 308 can be configured to combine the volume target site with the segmented anatomical structure and thus register the volume target site in the image spatial domain of the segmented anatomical structure to provide the co-registered image data 310. As disclosed herein, the co-registered image data 310 can be stored in memory and used to control a therapy delivery device or otherwise plan a procedure for delivery of a therapy or performing another intervention, such as a non-invasive ablation. The co-registered image data 310 can also be rendered on a display, such as superimposed on a 3D image generated based on the image data 304.

Figure 4:
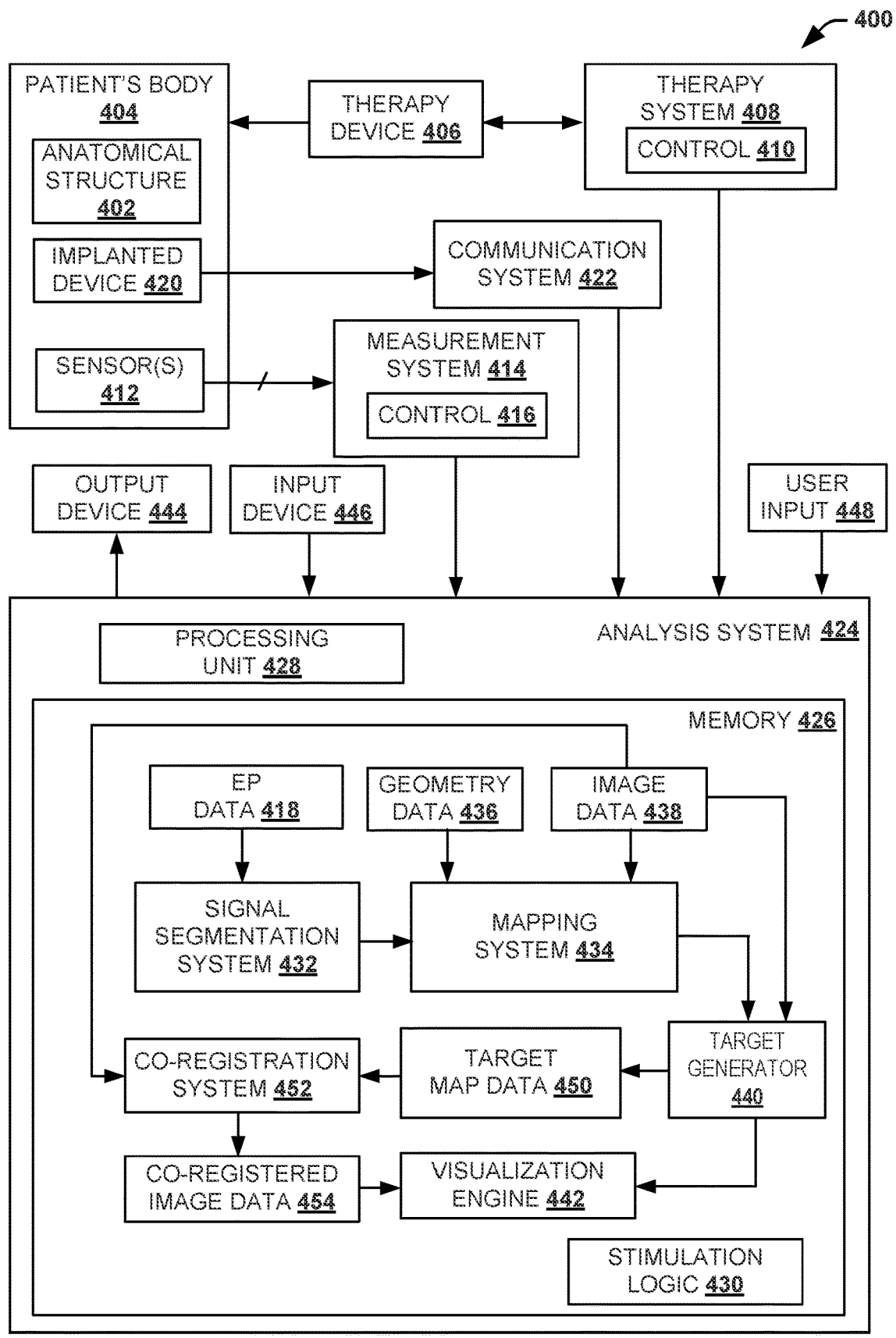
FIG. 4 is a block diagram of a treatment system.

FIG. 4 depicts an example of a system 400 that can be utilized for performing diagnostics and/or treatment of a patient, such as non-invasive ablation. In some examples, the system 400 can be implemented to generate corresponding maps (e.g., cardiac maps) for an anatomical structure 402 within a patient's body 404 in real time as part of a diagnostic procedure (e.g., an electrophysiology study) to help assess electrical activity and identify one or more target sites. Additionally, or alternatively, the system 400 can be utilized as part of a treatment procedure, such as to help a physician determine parameters for delivering a therapy to the patient (e.g., delivery location, amount, and type of therapy) based on one or more target sites identified according to the systems and methods disclosed herein.

For example, the patient's body 404 can be positioned relative to a therapy delivery device 406. By way of example, the therapy delivery device is a linear accelerator. The therapy delivery device 406 can be configured to deliver radiotherapy using gamma-rays or x-rays to each target site. As a further example, a therapy system 408 can be located external to the patient's body 404 and be configured to control therapy that is being delivered by the therapy delivery device 406 non-invasively as disclosed herein. For instance, the therapy system 408 includes controls (e.g., hardware and/or software) 410 that can be configured to communicate (e.g., supply) electrical signals via a conductive link electrically connected between the therapy delivery device and the therapy system 408. The controls 410 can control parameters of the therapy delivery device 406 (e.g., an amount of energy) for delivering the therapy (e.g., non-invasive ablation) to the identified target sites. The controls 410 can set therapy parameters and apply stimulation based on automatic, manual (e.g., user input), or a combination of automatic and manual (e.g., semiautomatic) controls. The position of the therapy delivery device 406 relative to the anatomical structure can be determined and/or tracked intraoperatively via a medical imaging modality (e.g., fluoroscopy, xray, ultrasound, and the like), direct vision, or a co-registered image as generated herein (e.g., the co-registered image data 310, as shown in FIG. 3), or the like.

Before, during and/or after delivering the therapy via the therapy system 408, another system or subsystem can be utilized to acquire electrophysiology information for the patient. In the example of FIG. 4, a sensor array 412 includes electrodes that can be utilized for measuring patient electrophysiological signals. As one example, the sensor array 412 can correspond to a high-density arrangement of body surface sensors (e.g., greater than approximately 50-200 electrodes) that are distributed over a portion of the patient's torso for measuring electrical activity associated with the anatomical structure (e.g., as part of an electrocardiographic mapping procedure), such as described above.

An example of a non-invasive sensor array that can be used is shown and described in International Application No. PCT/US2009/063803, filed 10 Nov. 2009. Other arrangements and numbers of sensing electrodes can be used as the sensor array 412. As an example, the array can be a reduced set of electrodes (e.g., a 12-Lead ECG), which does not cover the patient's entire torso and is designed for measuring electrical activity for a particular purpose (e.g., an array of electrodes specially designed for analyzing AF and/or VF) and/or for monitoring a predetermined spatial region of the heart. In some examples, one or more sensors may also be located on the therapy device 406. Such sensors can also be utilized to help localize the therapy delivery device 406 within the anatomical structure 402, which can be registered into an image or map that is generated by the system 400.

The sensor array 412 can be configured to provide the sensed electrical information to a corresponding measurement system 414. The measurement system 414 can include appropriate controls and signal processing circuitry and control 416 for providing corresponding electrophysiological data 418 (shown as "EP DATA" in FIG. 4) describing electrical activity measured by the sensors in the sensor array 412. The electrophysiological data 418 can include analog and/or digital information (e.g., corresponding to electrophysiological data 104, as shown in FIG. 1). A control 416 of the measurement system 414 can be configured to control the data acquisition process (e.g., sample rate, line filtering) for measuring electrical activity and providing the electrophysiological data 418. In some examples, the control 416 can control the acquisition of the electrophysiological data 418 separately from the therapy system operation, such as in response to a user input. In other examples, the electrophysiological data 418 can be acquired concurrently with and in synchronization with delivering therapy by the therapy system, such as to detect electrical activity of the anatomical structure 402 that occurs in response to applying a given therapy (e.g., according to therapy parameters). For instance, appropriate time stamps can be utilized for indexing the temporal relationship between the electrophysiological data 418 and therapy parameters used to deliver therapy to facilitate the evaluation and analysis thereof.

In some examples, a device (e.g., an implantable medical device) 420 is implanted within the patient's body 404. The implanted device 420 can communicate with a communication system 422. The implanted device 420 can be configured to communicate wirelessly with an analysis system 424 via the communication system 422. By way of example, the communication system 422 is a wireless system, such as a WiFi system (e.g., WiFi network). In some examples, the communication system 422 can be configured to allow for communication of data between the implanted device 420 and the analysis system 424 according to a wireless technology standard, such as near field communication (NFC), Bluetooth or WiFi standard.

The analysis system 424 can be implemented as including a computer, such as a laptop computer, a desktop computer, a server, a tablet computer, a workstation, or the like. The analysis system 424 can include memory 426 for storing data and machine-readable instructions. The memory 426 can be implemented, for example, as a non-transitory computer storage medium, such as volatile memory (e.g., random access memory), non-volatile memory (e.g., a hard disk drive, a solid-state drive, flash memory, or the like) or a combination thereof. The instructions can be programmed to perform one or more methods, such as disclosed herein with respect to the example of FIGS. 1-3. The analysis system 424 can include a processing unit 428 to access the memory 426 and execute the machine-readable instructions stored in the memory 426. The processing unit 428 could be implemented, for example, as one or more processor cores. In the present examples, although the components of the analysis system 424 are illustrated as being implemented on the same system, in other examples, the different components could be distributed across different systems and communicate, for example, over a network.

In some examples, the analysis system employs stimulation logic 430 to provide pacing parameters (e.g., pacing protocols) or other instructions to control the implanted device 420 via the communication system 422. In some examples, the communication system 422 communicates pacing parameters or other instructions through a wireless communications link. The link may be a direct link or an indirect link through a programmer device. The implanted device 420 can be configured to induce an electrophysiological event at the anatomical structure 402 based on the pacing parameters. Thus, in some examples, the implanted device 420 can be configured to induce a VT event at the anatomical structure 402. In additional examples, the implanted device 420 can be configured to terminate the induced an electrophysiological event at the anatomical structure 402 based on the pacing parameters. In some examples, the sensor array 412 can be configured to sense electrophysiological signals corresponding to the electrical activity at the anatomical structure 402 in response to the implanted device 420 inducing the electrophysiological event. In some examples, the electrophysiological event is not induced by the implanted device 420 and the patient is monitored via the sensor array 412 to capture the electrophysiological signals from the patient's body 404 for a natural occurrence of the electrophysiological event as well as other physiological conditions.

In some examples, the electrophysiological data 418 can be stored in the memory 426. The electrophysiological data 418 can be processed by a signal segmentation system 432 to identify each signal segment of interest in a same or similar manner as disclosed herein. Each signal segment of interest can represent a similar or a different electrophysiological event of the patient during a respective time interval. The signal segmentation system 432 can be implemented as the system 100, as shown in FIG. 1. The signal segmentation system 432 can be programmed to output signal segment data (e.g., the signal segment data 116, as shown in FIG. 1) to a mapping system 434. The mapping system 434 can correspond to the mapping system 204, as shown in FIG. 2.

The mapping system 434 can be programmed to reconstruct electrophysiological signals on a surface of interest of the anatomical structure 402 within the patient's body 404 based on non-invasively measured electrophysiological signals, including the signal segment data, and geometry data 436. The geometry data 436 can correspond to the geometry data 206, as shown in FIG. 2. Thus, the geometry data 436 can be a three-dimensional anatomical model of the anatomical structure 402 and the body surface where the electrophysiological signals are non-invasively measured. In some examples, the geometry data 436 can be derived from image data 438. The image data 438 can be provided by an imaging modality and can include one or more images of the anatomical structure 402 as disclosed herein.

The mapping system 434 can be programmed to compute an inverse solution to reconstruct electrophysiological signals on the surface of interest of the anatomical model of the anatomical structure 402 within the patient's body 404 based on the signal segment data and/or the electrophysiological data 418, and the geometry data 206. The mapping system 434 can be programmed to generate a map representing the reconstructed electrophysiological signals on the surface of interest for the respective time interval of the identified signal segment of interest. In some examples, an output generator can generate a graphical representation of the reconstructed electrophysiological signals that can be rendered on a display. The map can be provided as map data (e.g., the map data 208, as shown in FIG. 2) to a target generator 440. The target generator 440 can correspond to the target generator 218, as shown in FIG. 2. The target generator 440 thus can be programmed to identify a target site on the anatomical structure within the patient's body 404 based on the map data in a same or similar manner as disclosed herein.

For example, the target generator 440 can be programmed to identify each target site on the surface of interest of the anatomical model of the anatomical structure 402. In some examples, the target generator 440 can be programmed to communicate the map with each target site graphically differentiated therein as output data to a visualization engine 442. The visualization engine 442 can be configured to render the output data on an output device 444 (e.g., a display). In some examples, a user can employ an input device 446 (e.g., a keyboard, a mouse, and the like) to select each target site as a candidate target site for the therapy based on the visualization rendered on the output device 444. In some examples, the input device 446 can be used to provide user input data 448. The user input data 448 can identify each selected target site. In some examples, the user input data 448 can correspond to or include the user input data 108, as shown in FIG. 1 and/or the user input data 214, as shown in FIG. 2.

In some examples, the target generator 440 can be programmed to generate target map data 450. The target map data 450 can include the map with each target site (or candidate target site) identified therein. In some examples, the target map data 450 can be provided to the visualization engine 442, which can be programmed to render on the output device 444 the map with the target sites. By way of further example, the target generator 440 can be programmed to update the target site (or the candidate target site) to an updated target site based on one of the fiber orientation and the wall thickness of the anatomical structure 402 in a same or similar manner as disclosed herein. For example, the target generator 440 can be programmed to process the image data 438 to determine the fiber orientation and/or the wall thickness at a portion of the anatomical structure 402 that includes the surface of interest. The target generator 440 can be programmed to adjust the target site to the updated target site based on the fiber orientation and/or the wall thickness at portion of the anatomical structure 402.

In some examples, the target generator 440 can be programmed to combine (e.g., fuse) two or more maps computed based on different signal segments of interest over different time intervals to generate a fused (e.g., combined) map in a same or similar manner as disclosed herein. The target generator 440 can be programmed to identify target sites within each of the first and second maps. The target generator 440 can be programmed to combine the first and second maps to generate the fused map. In some examples, the target map data 450 can include the fused map with each target site differentiated, such as described herein, and can be used for treatment planning and delivery of the therapy (e.g., non-invasive ablation).

In some examples, the memory 426 include a co-registration system 452. The co-registration system 452 can correspond to the image-target registration system 300, as shown in FIG. 3. The co-registration system 452 can be programmed to register a target volume computed based on target map data 450 with the image data 438 provided by the imaging modality. The co-registration system 452 can be programmed to generate a volume target site for each target site, which may be differentiated on the map, based on the target map data 450 as disclosed herein. The co-registration system 452 can be programmed to register the volume target site in an image domain of the image data 438 to provide co-registered image data 454. The co-registered image data 454 can stored in the memory and transferred to the visualization engine 442 or to an external treatment system. The transfer may be direct through a network connection or it can be stored in a non-transitory medium and the medium can be physically transported and accessed by the visualization engine 442 or an external system. In some examples, the co-registration system 452 can be programmed to supply the co-registered image data 454 to the visualization engine 442. The visualization engine 442 can be configured to render on the output device 444 a visualization of the volume target site over one or more images of the anatomical structure 402 of the image data 438 for delivery of the therapy, as disclosed herein.

For example, the external system can be a treatment system, such as configured to perform treatment (e.g., non-invasive ablation) based on the co-registered image data 454. The external system can include the therapy device 406 for delivery of radiation to each target site identified in the co-registered image data 454. In some examples, the external system includes the output device 444 or another output device for visualization of the co-registered image data 454. A user (e.g., clinician) can employ the co-registered image data 454 rendered on the output device 444 or the other output device to delivery radiation therapy to each target site via the therapy device 406. An amount of radiation used for treating each target site can be determined by the external system, the user, or the analysis system 424.

Figure 5:
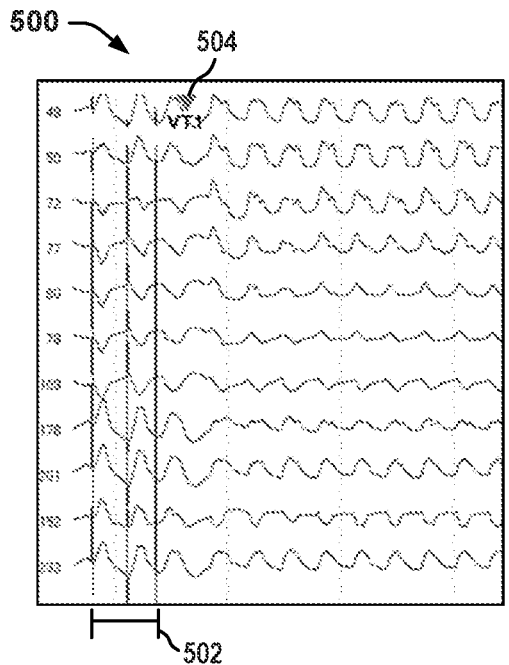
FIG. 5 is an example of a plot of measured electrophysiological signals.

FIG. 5 is an example of a plot 500 of electrophysiological signals. The electrophysiological signals can be measured from a human's body (e.g., via sensors distributed across a surface of a patient's body) as disclosed herein. Each of the measured electrophysiological signals can be provided as electrophysiological data (e.g., the electrophysiological data 104, as shown in FIG. 1) to a signal segment evaluator (e.g., the signal segment evaluator 102, as shown in FIG. 1). As disclosed herein, the signal segment evaluator can be configured to evaluate each of the electrophysiological signals to identify respective signal segments of interest therein representing an electrophysiological event of a patient during a respective time interval, as shown at 502 in the example of FIG. 5. By way of example, the electrophysiological event during the respective time interval 502 is a VT event 504. As disclosed herein, signal segment data (e.g., the signal segment data 116, as shown in FIG. 2) can be generated (e.g., by the signal segment extractor 114, as shown in FIG. 1) based on each identified signal segment of interest for inverse solution computation of reconstructed electrophysiological signals on a surface of interest within the patient's body.

Figure 6:
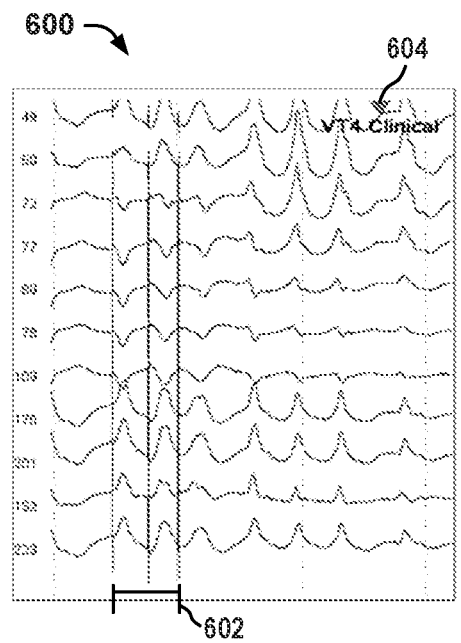
FIG. 6 is an example of another plot of measured electrophysiological signals.

FIG. 6 is an example of a plot 600 of electrophysiological signals. The electrophysiological signals can be measured from a human's body (e.g., via sensors distributed across a surface of a patient's body) as disclosed herein. Each of the measured electrophysiological signals can be provided as electrophysiological data (e.g., the electrophysiological data 104, as shown in FIG. 1) to a signal segment evaluator (e.g., the signal segment evaluator 102, as shown in FIG. 1). As disclosed herein, the signal segment evaluator can be configured to evaluate each of the electrophysiological signals to identify respective signal segments of interest therein representing an electrophysiological event of a patient during a respective time interval, as shown at 602 in the example of FIG. 6. By way of example, the electrophysiological event during the respective time interval 602 is a VT event 604. As disclosed herein, signal segment data (e.g., the signal segment data 116, as shown in FIG. 2) can be generated (e.g., by the signal segment extractor 114, as shown in FIG. 1) based on each identified signal segment of interest for inverse solution computation of reconstructed electrophysiological signals on a surface of interest within the patient's body.

Figure 7:
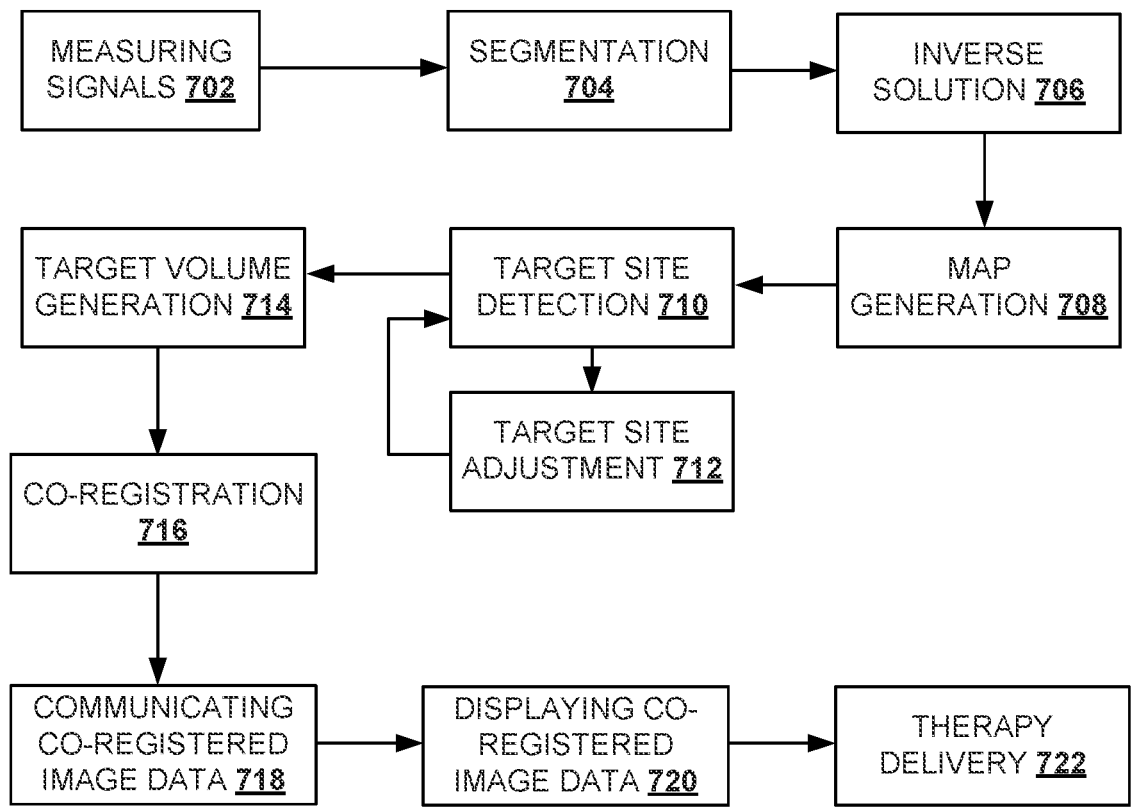
FIG. 7 is an example of a treatment delivery diagram.

FIG. 7 illustrates an example of a treatment delivery work flow diagram 700. The method shown in the diagram 700 can be implemented by the systems disclosed herein to perform non-invasive treatment of identified target sites. The work flow 700 can begin at 702 by measuring electrophysiological signals from a patient. As disclosed herein, the electrophysiological signals can be measured non-invasively and can be stored in memory (e.g., the memory 426, as shown in FIG. 1) as electrophysiological data (e.g., the electrophysiological data 104, as shown in FIG. 1). At 704, a morphology of at least one of the electrophysiological signals can be evaluated (e.g., by the signal segment evaluator 102, as shown in FIG. 1) to identify a signal segment of interest. The signal segment of interest can represent an electrophysiological event of the patient during a respective time interval, such as described herein. The signal segment of interest and/or the respective time interval for the signal segment of interest can be saved in memory as signal segment data (e.g., the signal segment data 116, as shown in FIG. 1).

At 706, an inverse solution can be applied to reconstruct electrophysiological signals on a surface of interest within a body of a patient based on the signal segment data and/or the electrophysiological signal data, and geometry data (e.g., the geometry data 206, as shown in FIG. 2). The geometry data can include three-dimensional spatial data for the surface of interest and the body surface where the electrophysiological signals are measured. In an example, the geometry data is computed based on image data (e.g., the image data 210, as shown in FIG. 2) generated by an imaging modality. The image data can includes one or more images of an anatomical structure within the patient. At 708, a map can be generated (e.g., by the map generator 216, as shown in FIG. 2) representing the reconstructed electrophysiological signals on the surface of interest for the respective time interval of the identified signal segment of interest. At 710, a target site within the patient's body can be identified (e.g., by the target generator 218, as shown in FIG. 2) based on the map for the electrophysiological event. The map with the identified target site can be stored in memory as target map data (222, as shown in FIG. 2). Each target site on the map can be differentiated from each other and from surrounding regions of the surface of interest.

In some examples, at 712, the target site can be updated (e.g., by the target site adjuster 224, as shown in FIG. 2) based one of fiber orientation and/or wall thickness at a portion of an anatomical structure that includes the surface of interest. As described herein, the fiber orientation and/or wall thickness can be determined from the image data that is used for computing the geometry data. In some examples, at 714, a volume target site for each target site (or each updated target site) can be generated (e.g., by the target volume generator 306, as shown in FIG. 3). At 716, the volume target site can be registered (e.g., by the co-registration engine 308, as shown in FIG. 3) with a segmented anatomical structure from the image data to provide co-registered image data (e.g., the co-registered image data 310, as shown in FIG. 3).

At 718, the co-registered image data can be communicated to an external system. For example, the co-registered image data can be communicated (e.g., by the analysis system 424, as shown in FIG. 4) over a network (e.g., wired, wireless, or a combination thereof) to the external system. In some examples, the co-registered image data can be stored on a portable non-transitory medium (e.g., flash drive) that can be provided to the external system. In other examples, the co-registered image data can be stored on a network or in a cloud environment that the external system can access to retrieve the stored co-registered image data. At 720, the co-registered image data can be rendered on a display (e.g., by the visualization engine 442, as shown in FIG. 4) to provide visual guidance for delivery of a therapy to the patient. At 722, non-invasive ablation therapy can be delivered (e.g., via therapy device 406, as shown in FIG. 1) to the patient based on each target site on the surface of interest.

Figure 8:
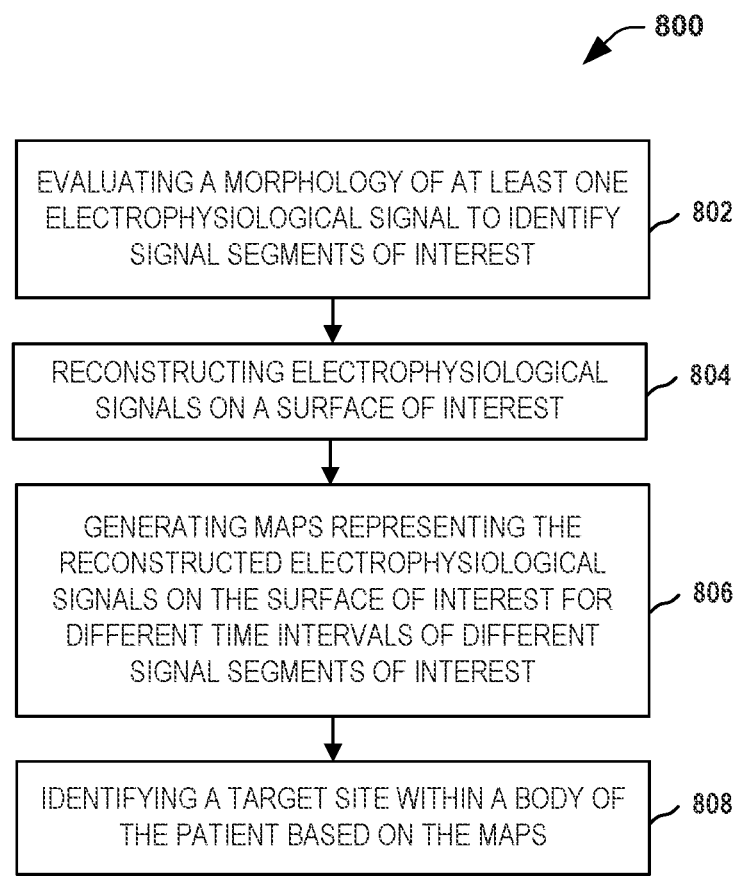
FIG. 8 is a flow diagram that illustrates a method for identifying a target site within a body of a patient.

In view of the foregoing structural and functional features described above, an example method will be better appreciated with reference to FIG. 8. While, for purposes of simplicity of explanation, the example method of FIG. 8 is shown and described as executing serially, it is to be understood and appreciated that the example method is not limited by the illustrated order, as some actions could in other examples occur in different orders, multiple times and/or concurrently from that shown and described herein.

FIG. 8 illustrates an example of a method 800 for identifying a target site within a body of a patient for non-invasive therapy. The method 800 can be implemented by the systems disclosed herein. Therefore, references can be made to the example of FIGS. 1-4 in the following description of the example of FIG. 8. The method 800 can begin at 802 by evaluating (e.g., via the signal segment evaluator 102, as shown in FIG. 1) a morphology of at least one electrophysiological signal of a plurality of electrophysiological signals measured from an outer surface of a patient's body to identify first and second signal segments of interest. The morphology of the first signal segment of interest can be indicative of an electrophysiological event of the patient during a first time interval. The morphology of the second signal segment of interest can be indicative of an electrophysiological event of the patient during a second time interval. At 804, reconstructing (via the reconstruction engine 212, as shown in FIG. 2) electrophysiological signals on a surface of interest within a body of the patient based on the electrophysiological signals and geometry data (e.g., the geometry data 206, as shown in FIG. 2). The geometry data can represent an anatomy of the patient.

At 806, generating a first map representing the reconstructed electrophysiological signals on the surface of interest for the first time interval of the first signal segment of interest. At 808, generating a second map representing the reconstructed electrophysiological signals on the surface of interest for the second time interval of the second signal segment of interest. Each of the first and second maps can be generated by the map generator 216, as shown in FIG. 2, and can be stored in memory (e.g., the memory 426, as shown in FIG. 4) as target map data (e.g., the target map data 450, as shown in FIG. 4). At 810, identifying a target site within the patient's body based on the first and second maps for the electrophysiological event. The target site can be identified by the target generator 440, as shown in FIG. 4. As disclosed herein, the target site can be used for delivering of non-invasive ablation therapy.

It should be understood that various aspects disclosed herein may be combined in different combinations than the combinations specifically presented in the description and accompanying drawings. It should also be understood that, depending on the example, certain acts or events of any of the processes or methods described herein may be performed in a different sequence, may be added, merged, or left out altogether (e.g., all described acts or events may not be necessary to carry out the techniques). In addition, while certain aspects of this disclosure are described as being performed by a single module or unit for purposes of clarity, it should be understood that the techniques of this disclosure may be performed by a combination of units or modules associated with, for example, a medical device.

In one or more examples, the described techniques may be implemented in hardware, software, firmware, or any combination thereof. If implemented in software, the functions may be stored as one or more instructions or code on a computer-readable medium and executed by a hardware-based processing unit. Computer-readable media may include non-transitory computer-readable media, which corresponds to a tangible medium such as data storage media (e.g., RAM, ROM, EEPROM, flash memory, or any other medium that can be used to store desired program code in the form of instructions or data structures and that can be accessed by a computer).

Instructions may be executed by one or more processors, such as one or more digital signal processors (DSPs), general purpose microprocessors, application specific integrated circuits (ASICs), field programmable logic arrays (FPGAs), or other equivalent integrated or discrete logic circuitry. Accordingly, the term "processor" as used herein may refer to any of the foregoing structure or any other physical structure suitable for implementation of the described techniques. Also, the techniques could be fully implemented in one or more circuits or logic elements.

Additionally, where the disclosure or claims recite "a," "an," "a first," or "another" element, or the equivalent thereof, it should be interpreted to include one or more than one such element, neither requiring nor excluding two or more such elements. As used herein, the term "includes" means includes but not limited to, and the term "including" means including but not limited to. The term "based on" means based at least in part on.

What is claimed is:

1. One or more non-transitory computer-readable media having data and machine readable instructions executable by a processor, the data comprising electrophysiological data representing electrophysiological signals measured from an outer surface of a patient's body and geometry data representing an anatomy of the patient, the machine readable instructions comprising:
a signal segment evaluator programmed to sample one or more portions of at least one of the electrophysiological signals and evaluate a morphology of the one or more sampled portions to identify a signal segment of interest, wherein a morphology of the signal segment of interest is indicative of an electrophysiological event of the patient during a respective time interval;
a signal segment extractor programmed to extract the signal segment of interest from the at least one of the electrophysiological signals to provide signal segment data in response to identifying the signal segment of interest, the signal segment data identifying the respective time interval during which the signal segment of interest occurred;
a reconstruction engine programmed to reconstruct electrophysiological signals on a surface of interest within a body of the patient based on the signal segment data, the electrophysiological data, and the geometry data;
a map generator programmed to generate a map representing the reconstructed electrophysiological signals on the surface of interest for the respective time interval of the signal segment of interest; and
a target generator programmed to identify a target site within the patient's body based on the map for the electrophysiological event.

2. The one or more non-transitory computer-readable media of claim 1, wherein the reconstruction engine is programmed to reconstruct the electrophysiological signals on the surface of interest within the patient's body based on the electrophysiological data representing the electrophysiological signals for the respective time interval of the signal segment of interest.

3. The one or more non-transitory computer-readable media of claim 2, wherein the signal segment evaluator is programmed to sample one or more portions of each remaining electrophysiological signal of the electrophysiological signals for the respective time interval and evaluate a morphology of the one or more sampled portions of each remaining electrophysiological signal to identify a sampled portion from each remaining electrophysiological signal, each identified sampled portion corresponding to a respective signal segment of interest from a remaining electrophysiological signal, wherein a morphology of each respective signal segment of interest is indicative of the electrophysiological event of the patient during the respective time interval.

4. The one or more non-transitory computer-readable media of claim 3, wherein the reconstruction engine is programmed to reconstruct the electrophysiological signals on the surface of interest within the body of the patient based on the respective signal segment of interest from each remaining electrophysiological signal and the signal segment of interest from the at least one electrophysiological signal.

5. The one or more non-transitory computer-readable media of claim 4, wherein the signal segment evaluator is programmed to compare each sampled portion of each electrophysiological signal to a signal segment library to identify the signal segment of interest of the at least one electrophysiological signal and the respective signal segment of interest from each remaining electrophysiological signal.

6. The one or more non-transitory computer-readable media of claim 5, wherein the signal segment evaluator is programmed to apply a moving window to the at least one electrophysiological signal to sample the one or more portions of the at least one electrophysiological signal and compare each sampled portion of the at least one electrophysiological signal to the signal segment library to identify the signal segment of interest.

7. The one or more non-transitory computer-readable media of claim 4, wherein the electrophysiological event is induced by a device implanted in the body of the patient.

8. The one or more non-transitory computer-readable media of claim 7, wherein the signal segment evaluator programmed to identify a portion of the at least one electrophysiological signal as the signal segment of interest based on time at which the electrophysiological event was induced by the device.

9. The one or more non-transitory computer-readable media of claim 4, wherein the electrophysiological event includes one of an arrhythmia event.

10. The one or more non-transitory computer-readable media of claim 4, wherein the map generator is programmed to reconstruct the electrophysiological signals on the surface of interest of an anatomical model of an anatomical structure, the anatomical model being generated based on the geometry data.

11. The one or more non-transitory computer-readable media of claim 10, wherein the target generator is programmed to identify each target site based on user input data identifying each target site on the map representing reconstructed electrophysiological signals on the surface of interest for the respective time interval of the identified signal segment of interest.

12. The one or more non-transitory computer-readable media of claim 10, wherein the target generator comprises a machine learning (ML) module, the ML module being programmed to evaluate the map representing reconstructed electrophysiological signals on the surface of interest for the respective time interval of the identified signal segment of interest to identify each target site.

13. The one or more non-transitory computer-readable media of claim 10, wherein the map comprises one of a butterfly map, a phase map, a propagation map, an activation map, a potential map or other electrophysiology map derived based on the electrophysiological signals.

14. The one or more non-transitory computer-readable media of claim 13, wherein the map corresponds to a plurality of different types of maps representing the reconstructed electrophysiological signals on the surface of interest for the respective time interval of the signal segment of interest, the target generator being programmed to identify electrophysiological event features from each of the plurality of different types of maps and identify the target site within the patient's body based on the identified electrophysiological event features.

15. The one or more non-transitory computer-readable media of claim 10, wherein the signal segment of interest is a first signal segment of interest and the respective time interval is a first time interval, and the signal segment evaluator is programmed to evaluate the morphology of the at least one of the electrophysiological signals to identify a second signal segment of interest, the morphology of the second signal segment of interest being indicative of the electrophysiological event of the patient during a second time interval.

16. The one or more non-transitory computer-readable media of claim 15, wherein the map is a first map, the reconstruction engine being programmed to reconstruct electrophysiological signals on the surface of interest within the body of the patient based on the electrophysiological data representing the electrophysiological signals for the second time interval of the second signal segment of interest, the map generator being programmed to generate a second map representing the reconstructed electrophysiological signals on the surface of interest for the second time interval of the second signal segment of interest.

17. The one or more non-transitory computer-readable media of claim 16, wherein the target site is a first target site and the target generator is programmed to identify a second target site within the patient's body based on the second map for the electrophysiological event.

18. The one or more non-transitory computer-readable media of claim 17, further comprising a map fusion engine programmed to combine the first and second maps to provide a map with a composite target site for the electrophysiological event.

19. The one or more non-transitory computer-readable media of claim 16,
wherein the target site is a first target site,
wherein the first map comprises is a first set of maps representing the reconstructed electrophysiological signals on the surface of interest for the first time interval of the first signal segment of interest,
wherein the second map comprises is a second set of maps representing the reconstructed electrophysiological signals on the surface of interest for the second time interval of the second signal segment of interest,
the target generator being programmed to identify electrophysiological event features from the first set of maps and identify the first target site within the patient's body based on the identified electrophysiological event feature from the first set of maps,
the target generator being programmed to identify electrophysiological event features from the second set of maps and identify a second target site within the patient's body based on the identified electrophysiological event feature from the second set of maps, and
further comprising a map fusion engine programmed to combine the first and second maps to provide a map with a composite target site for the electrophysiological event.

20. The one or more non-transitory computer-readable media of claim 19, wherein each of the first and second set of maps comprises at least two of a butterfly map, a phase map, a propagation map, and an activation map or other electrophysiology map derived from the reconstructed electrophysiological signals.

21. The one or more non-transitory computer-readable media of claim 19, further comprising a target site adjuster programmed to update the composite target site for the electrophysiological event to an updated composite target site based on one of a fiber orientation and a wall thickness at an anatomical location of the anatomical structure for the composite target site, the fiber orientation and the wall thickness at the anatomical location of the anatomical structure being determined based on imaging data provided by an imaging modality.

22. A system comprising:
a plurality of sensors configured to measure electrophysiological signals from an outer surface of a patient's body;
memory configured to store machine readable instructions and data comprising electrophysiological data representing the electrophysiological signals and geometry data representing an anatomy of the patient;
at least one processor configured to access the memory and configured to execute the machine readable instructions, the machine readable instructions comprising:
a signal segment evaluator programmed to sample one or more portions of at least one of the electrophysiological signals and evaluate a morphology of the one or more sampled portions to identify a signal segment of interest, wherein a morphology of the signal segment of interest is indicative of an electrophysiological event of the patient during a respective time interval;
a signal segment extractor programmed to extract the signal segment of interest from the at least one of the electrophysiological signals to provide signal segment data in response to identifying the signal segment of interest, the signal segment data identifying the respective time interval during which the signal segment of interest occurred;
a reconstruction engine is programmed to reconstruct electrophysiological signals on a surface of interest within the patient's body based on the signal segment data, the electrophysiological data representing the electrophysiological signals for the respective time interval of the signal segment of interest, and the geometry data;
a map generator programmed to generate a map representing the reconstructed electrophysiological signals on the surface of interest for the respective time interval of the signal segment of interest; and
a target generator programmed to identify a target site within the patient's body based on the map for the electrophysiological event.

23. The system of claim 22,
wherein the signal segment evaluator is programmed to sample one or more portions of each remaining electrophysiological signal of the electrophysiological signals for the respective time interval and evaluate a morphology of the one or more sampled portions of each remaining electrophysiological signal to identify a respective signal segment of interest from each remaining electrophysiological signal, wherein a morphology of each remaining signal segment of interest is indicative of the electrophysiological event of the patient during the respective time interval, and
wherein the reconstruction engine is programmed to reconstruct the electrophysiological signals on the surface of interest within the patient's body based on the respective signal segment of interest from each remaining electrophysiological signal and the signal segment of interest from the at least one electrophysiological signal.

24. The system of claim 23, wherein the signal segment evaluator is programmed to compare each sampled portion of each electrophysiological signal to a signal segment library to identify the signal segment of interest of the at least one electrophysiological signal and the respective signal segment of interest from each remaining electrophysiological signal.

25. The system of claim 24, wherein the target generator is programmed to identify each target site based on one of:
user input data identifying each target site on the map representing reconstructed electrophysiological signals on the surface of interest for the respective time interval of the identified signal segment of interest; and
a machine learning module being trained to evaluate the map representing reconstructed electrophysiological signals on the surface of interest for the respective time interval of the identified signal segment of interest.

26. The system of claim 25, wherein the map corresponds to a plurality of different types of maps representing the reconstructed electrophysiological signals on the surface of interest for the respective time interval of the signal segment of interest, the target generator being programmed to identify electrophysiological event features from each of the plurality of different types of maps and identify the target site within the patient's body based on the identified electrophysiological event features.

27. The system of claim 25, wherein the signal segment of interest is a first signal segment of interest and the respective time interval is a first time interval, and the signal segment evaluator is programmed to evaluate the morphology of the at least one of the electrophysiological signals to identify a second signal segment of interest, the morphology of the second signal segment of interest being indicative of the electrophysiological event of the patient during a second time interval.

28. The system of claim 27, wherein the map is a first map, the reconstruction engine being programmed to reconstruct electrophysiological signals on the surface of interest within the patient's body based on the electrophysiological data representing the electrophysiological signals for the second time interval of the second signal segment of interest, the map generator being programmed to generate a second map representing the reconstructed electrophysiological signals on the surface of interest for the second time interval of the second signal segment of interest.

29. The system of claim 28,
wherein the target site is a first target site and the target generator is programmed to identify a second target site within the patient's body based on the second map for the electrophysiological event, and
the machine readable instructions further comprising a map fusion engine programmed to combine the first and second maps to provide a map with a composite target site for the electrophysiological event.

30. The system of claim 26,
wherein the target site is a first target site,
wherein the first map comprises is a first set of maps representing the reconstructed electrophysiological signals on the surface of interest for the first time interval of the first signal segment of interest,
wherein the second map comprises is a second set of maps representing the reconstructed electrophysiological signals on the surface of interest for the second time interval of the second signal segment of interest,
the target generator being programmed to identify electrophysiological event features from the first set of maps and identify the first target site within the patient's body based on the identified electrophysiological event feature from the first set of maps,
the target generator being programmed to identify electrophysiological event features from the second set of maps and identify a second target site within the patient's body based on the identified electrophysiological event feature from the second set of maps, and
the machine readable instructions further comprising a map fusion engine programmed to combine the first and second maps to provide a map with a composite target site for the electrophysiological event.

31. A computer-implemented method comprising:
sampling portions of at least one electrophysiological signal of a plurality of electrophysiological signals measured from an outer surface of a patient's body;
evaluating a morphology of the sampled portions to identify first and second signal segments of interest, wherein a morphology of each of the first and second signal segments of interest is indicative of an electrophysiological event of the patient during one of a first time interval and a second time interval;
extracting the first and second signal segments of interest from the at least one of the electrophysiological signals to provide signal segment data in response to identifying the first and second signal segments of interest, the signal segment data identifying the first and second time intervals during which a corresponding one of the first and second signal segments occurred;
reconstructing electrophysiological signals on a surface of interest within a body of the patient based on the electrophysiological signals, the signal segment data and geometry data, the geometry data representing an anatomy of the patient;
generating a first map representing the reconstructed electrophysiological signals on the surface of interest for the first time interval of the first signal segment of interest;
generating a second map representing the reconstructed electrophysiological signals on the surface of interest for the second time interval of the second signal segment of interest; and
identifying a target site within the patient's body based on the first and second maps for the electrophysiological event.

32. The computer-implemented method of claim 31, wherein the evaluating of the morphology of the sampled portions comprises comparing each sampled portion to a signal segment library to identify the first and second signal segments of interest.

33. The computer-implemented method of claim 32,
wherein the target site is a composite target site,
wherein the first map comprises a first set of maps and the second map comprises a second set of maps,
wherein identifying the target site comprises:
identifying first electrophysiological event features from each of the first set of maps and identifying a first target site within the patient's body based on the first electrophysiological event features identified from each of the first set of maps;
identifying second electrophysiological event features from each of the second set of maps and identifying a second target site within the patient's body based on the second electrophysiological event features identified from each of the second set of maps; and
identifying the composite target site based on the first and second target sites for the electrophysiological event.

34. The computer-implemented method of claim 32,
wherein the target site is a composite target site,
wherein identifying the target site comprises:

identifying a first target site within the patient's body based on the first map for the electrophysiological event;

identifying a second target site within the patient's body based on the second map for the electrophysiological event; and combining the first and second maps to provide a map with a composite target site for the electrophysiological event.

35. The computer-implemented method of claim 31, wherein each of the first and second set of maps comprises at least two of a butterfly map, a phase map, a propagation map, and an activation map, or other electrophysiology map derived based on the electrophysiological signals.

36. The computer-implemented method of claim 34, further comprising updating the composite target site for the electrophysiological event to an updated composite target site based on one of a fiber orientation and a wall thickness at an anatomical location of the anatomy for the composite target site, the fiber orientation and the wall thickness at the anatomical location of the anatomy being determined based on imaging data provided by an imaging modality.

\* \* \* \* \*